(12) United States Patent
Donahoe et al.

(10) Patent No.: US 7,451,870 B2
(45) Date of Patent: Nov. 18, 2008

(54) MEDICAL IMPLANT PACKAGE WITH A CAP HAVING A CAVITY

(75) Inventors: Ryan M. Donahoe, San Diego, CA (US); Nathan J. Meyer, Vista, CA (US); Thomas H. Day, Carlsbad, CA (US); Christopher M. Gervais, San Marcos, CA (US); Fred Murillo, San Diego, CA (US)

(73) Assignee: Zimmer Dental, Inc., Carlsbad, CA (US)

( * ) Notice: Subject to any disclaimer, the term of this patent is extended or adjusted under 35 U.S.C. 154(b) by 82 days.

(21) Appl. No.: 11/347,987

(22) Filed: Feb. 6, 2006

(65) Prior Publication Data

US 2007/0181446 A1    Aug. 9, 2007

(51) Int. Cl.
*A61B 19/02* (2006.01)
*B65D 51/04* (2006.01)
*B65D 83/10* (2006.01)
*B65D 85/00* (2006.01)

(52) U.S. Cl. ............... 206/63.5; 206/369; 220/521; 220/819; 220/826

(58) Field of Classification Search .......... 206/63.5, 206/368; 220/521–522, 819, 826; 433/141, 433/172–177
See application file for complete search history.

(56) References Cited

U.S. PATENT DOCUMENTS

| | | | |
|---|---|---|---|
| 3,462,034 A | 8/1969 | Friedberg |
| 3,890,204 A | 6/1975 | Avery |
| 3,904,058 A | 9/1975 | Rosenstein |
| 3,981,398 A | 9/1976 | Boshoff |
| 4,027,392 A | 6/1977 | Sawyer et al. |
| 4,364,473 A | 12/1982 | Bogaert |
| 4,445,611 A | 5/1984 | Shofu |

(Continued)

FOREIGN PATENT DOCUMENTS

EP    0 66 9111 A2    8/1995

(Continued)

OTHER PUBLICATIONS

Spline Twist MP-1, Sulzer Calcitek Inc. Copyright 1998.

(Continued)

*Primary Examiner*—Bryon P Gehman
(74) *Attorney, Agent, or Firm*—Fitch, Even, Tabin & Flannery

(57) ABSTRACT

A medical implant package including a vial and a cap connected by a hinge. The vial includes a cavity for housing at least a portion of a dental implant. To access the implant, the cap is rotated about the hinge from a closed position to an open position. The cap defines a second cavity, separate from the vial cavity, sized to contain a healing screw. In one embodiment, the cap includes two portions connected by a living hinge which define the second cavity. The two cap portions, when moved relative to each other via the living hinge, permit access to the healing screw. In an alternative embodiment, the cap includes two retention members sized and configured to grip the healing screw. To remove the healing screw from the cap, the two retention members are displaced apart from each other by engaging them with a wedge extending from the vial.

13 Claims, 10 Drawing Sheets

U.S. PATENT DOCUMENTS

| | | | |
|---|---|---|---|
| 4,475,654 A * | 10/1984 | Fruchter | 220/521 |
| 4,615,462 A | 10/1986 | Sacherer et al. | |
| 4,666,037 A | 5/1987 | Weissman | |
| 4,671,410 A | 6/1987 | Hansson et al. | |
| 4,697,703 A | 10/1987 | Will | |
| 4,712,681 A | 12/1987 | Brånemark et al. | |
| 4,717,018 A | 1/1988 | Sacherer et al. | |
| 4,763,788 A | 8/1988 | Jörnéus et al. | |
| 4,809,874 A | 3/1989 | Pehr | |
| 4,856,648 A | 8/1989 | Krueger | |
| 4,867,305 A | 9/1989 | Schneider | |
| 4,874,088 A | 10/1989 | Leben | |
| 4,934,556 A * | 6/1990 | Kleissendorf | 220/522 |
| 4,942,991 A | 7/1990 | Lyons | |
| 4,948,000 A | 8/1990 | Grabenkort | |
| 4,953,705 A | 9/1990 | Evamy | |
| 4,966,465 A | 10/1990 | Randklev | |
| 4,978,007 A | 12/1990 | Jacobs et al. | |
| 4,982,769 A | 1/1991 | Fournier et al. | |
| 5,013,238 A | 5/1991 | Sterrett et al. | |
| 5,062,800 A | 11/1991 | Niznick | |
| 5,069,366 A | 12/1991 | Graffin | |
| 5,117,976 A | 6/1992 | Whitt et al. | |
| 5,197,881 A | 3/1993 | Chalifoux | |
| 5,270,011 A | 12/1993 | Altherr | |
| 5,358,130 A | 10/1994 | Mengeu et al. | |
| 5,368,160 A | 11/1994 | Leuschen et al. | |
| 5,409,377 A | 4/1995 | Mays | |
| 5,429,229 A | 7/1995 | Chester et al. | |
| 5,437,550 A | 8/1995 | Beaty et al. | |
| 5,462,436 A | 10/1995 | Beaty | |
| 5,538,428 A | 7/1996 | Staubli | |
| 5,558,230 A | 9/1996 | Fischer et al. | |
| 5,564,924 A | 10/1996 | Kwan | |
| 5,575,645 A | 11/1996 | Jacobs et al. | |
| 5,582,299 A | 12/1996 | Lazzara et al. | |
| 5,607,050 A | 3/1997 | Dolan et al. | |
| 5,622,500 A | 4/1997 | Niznick | |
| 5,636,736 A | 6/1997 | Jacobs et al. | |
| 5,636,911 A | 6/1997 | Korpi | |
| 5,636,991 A | 6/1997 | Mays | |
| 5,667,094 A | 9/1997 | Rapchak et al. | |
| 5,692,609 A | 12/1997 | Lin | |
| 5,692,904 A | 12/1997 | Beaty | |
| 5,711,468 A | 1/1998 | Shoemaker | |
| 5,733,124 A | 3/1998 | Kwan | |
| 5,752,603 A | 5/1998 | Faber | |
| 5,755,575 A | 5/1998 | Biggs | |
| 5,860,760 A | 1/1999 | Kirk | |
| 5,927,979 A | 7/1999 | Misch et al. | |
| 5,961,330 A | 10/1999 | Hanson | |
| 5,964,591 A | 10/1999 | Beaty et al. | |
| 5,967,305 A | 10/1999 | Blonder et al. | |
| 5,996,779 A | 12/1999 | Klardie et al. | |
| 6,068,480 A | 5/2000 | Misch et al. | |
| 6,076,660 A | 6/2000 | Day | |
| D427,906 S * | 7/2000 | Carter | D9/436 |
| 6,083,004 A | 7/2000 | Misch et al. | |
| 6,086,371 A | 7/2000 | Bassett et al. | |
| 6,142,296 A | 11/2000 | Klardie et al. | |
| 6,152,304 A | 11/2000 | Hikita et al. | |
| 6,164,442 A * | 12/2000 | Stravitz | 220/522 |
| 6,203,323 B1 | 3/2001 | Beaty et al. | |
| 6,217,332 B1 | 4/2001 | Kumar | |
| 6,247,932 B1 | 6/2001 | Sutter | |
| RE37,252 E | 7/2001 | Hollister | |
| 6,261,097 B1 | 7/2001 | Schmutz et al. | |
| 6,280,192 B1 | 8/2001 | Groll et al. | |
| 6,428,318 B2 | 8/2002 | Artal | |
| 6,464,500 B1 | 10/2002 | Popovic | |
| 6,561,805 B2 | 5/2003 | Kumar | |
| 6,619,958 B2 | 9/2003 | Beaty et al. | |
| 6,913,465 B2 | 7/2005 | Howlett et al. | |
| 6,955,258 B2 | 10/2005 | Howlett et al. | |
| 2001/0054563 A1 | 12/2001 | Lang et al. | |
| 2002/0107127 A1 | 8/2002 | Buisson et al. | |
| 2002/0117500 A1 | 8/2002 | Buisson et al. | |
| 2002/0170915 A1 * | 11/2002 | Hierzer | 220/521 |
| 2003/0221977 A1 | 12/2003 | Kumar et al. | |
| 2003/0224326 A1 | 12/2003 | Day et al. | |
| 2004/0043358 A1 | 3/2004 | Howlett et al. | |
| 2004/0096804 A1 | 5/2004 | Vogt et al. | |
| 2004/0112781 A1 | 6/2004 | Hofverberg et al. | |
| 2005/0023166 A1 | 2/2005 | Howlett et al. | |

FOREIGN PATENT DOCUMENTS

| | | |
|---|---|---|
| EP | 1087719 | 2/2003 |
| FR | 2746629 | 10/1997 |
| WO | WO9965416 | 12/1999 |
| WO | WO02098744 | 12/2002 |
| WO | WO03059190 | 7/2003 |

OTHER PUBLICATIONS

Confidential internal Zimmer drawing—a product made in accordance therewith may have been commercialized.

* cited by examiner

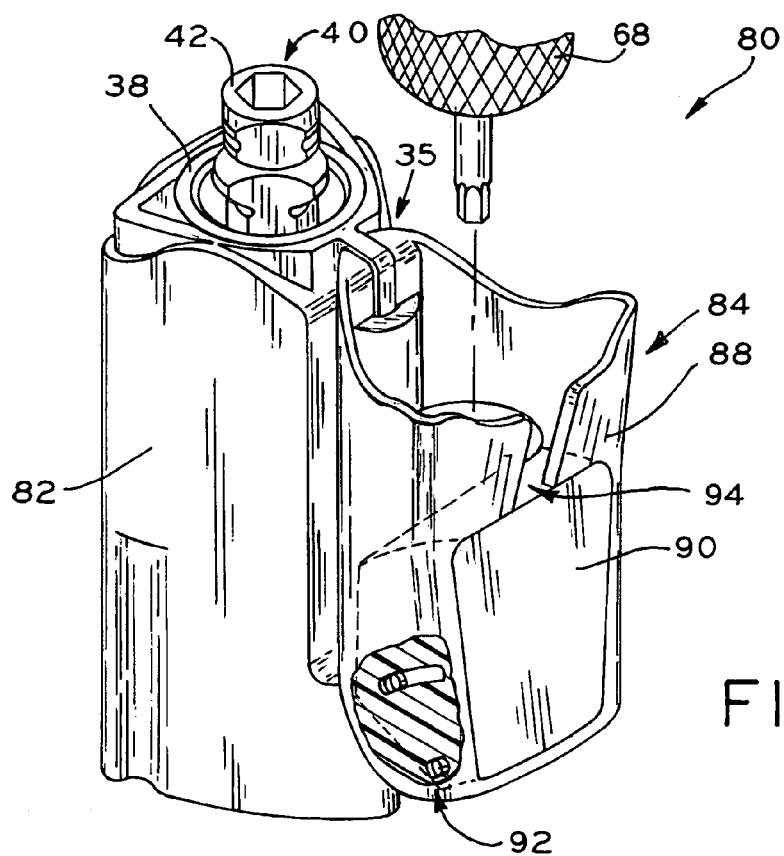
FIG_5
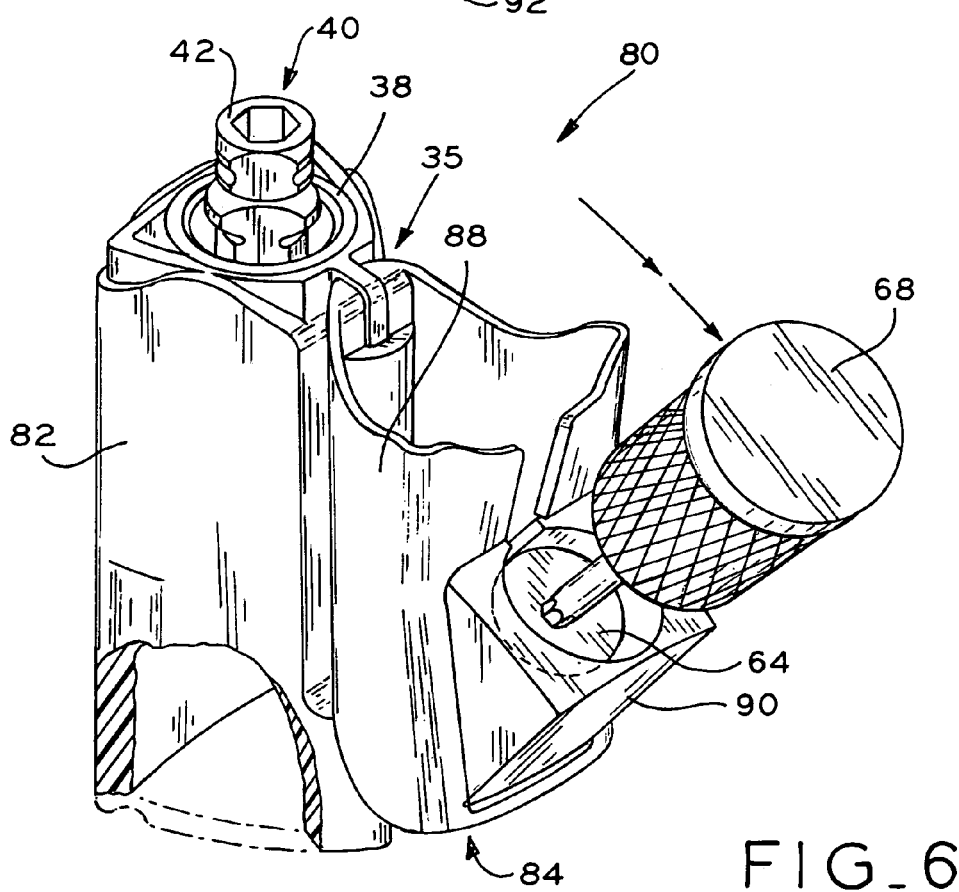
FIG_6

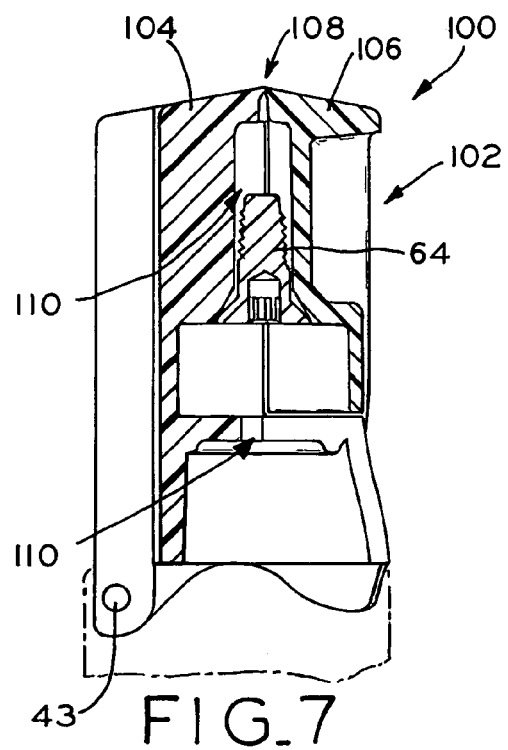
FIG_7
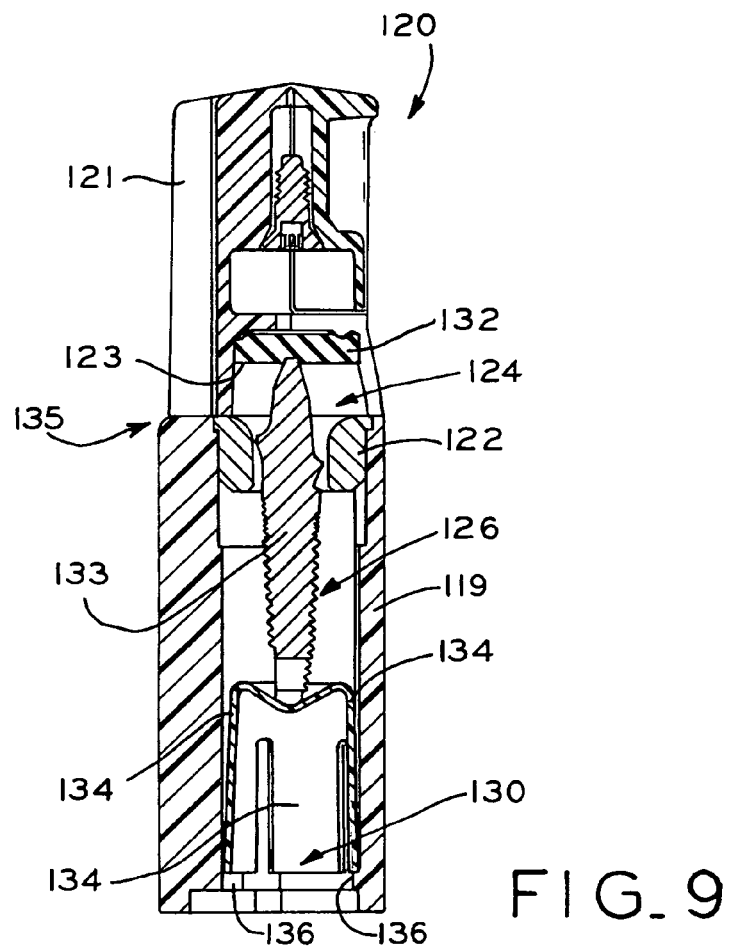
FIG_9

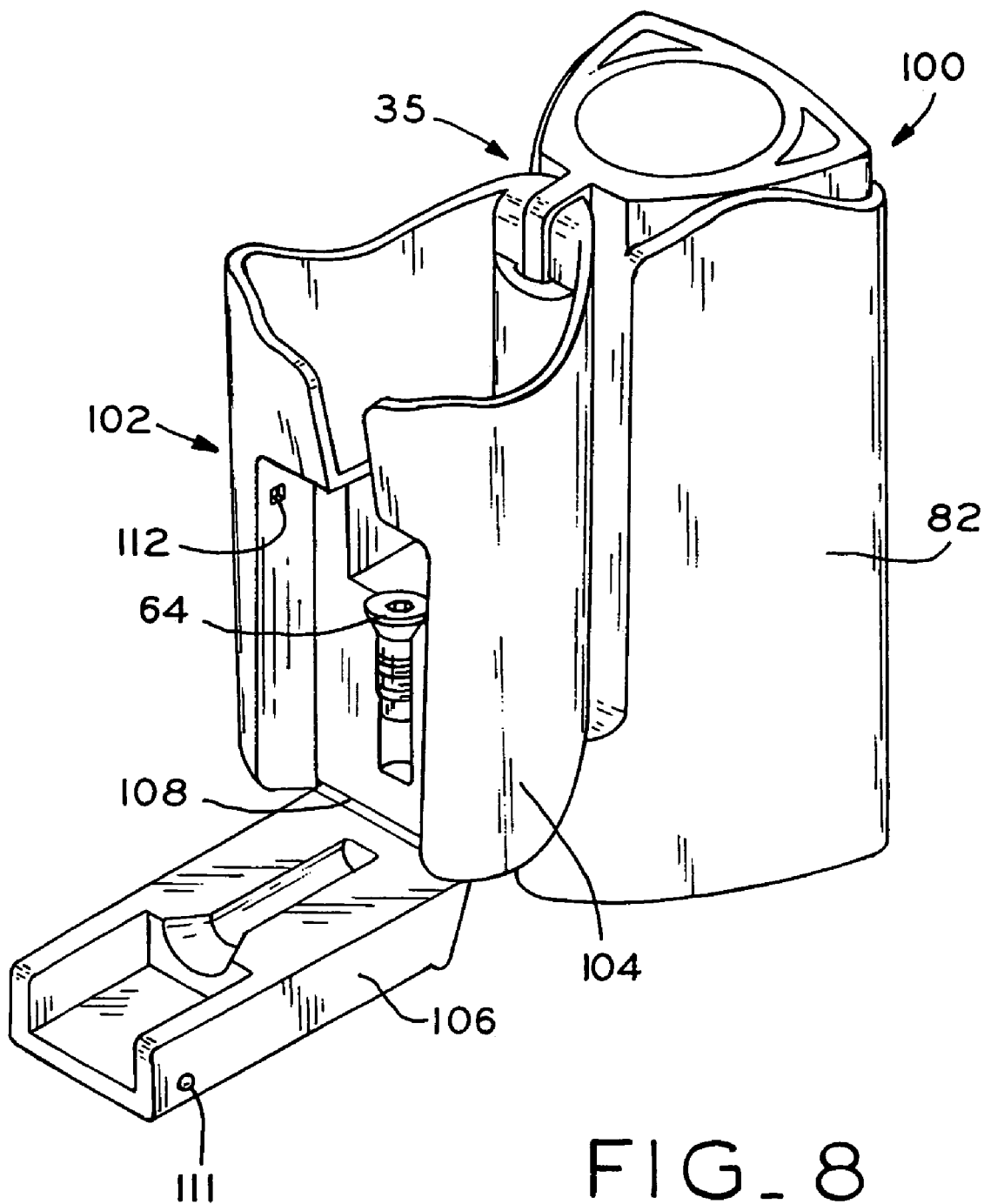
FIG_8

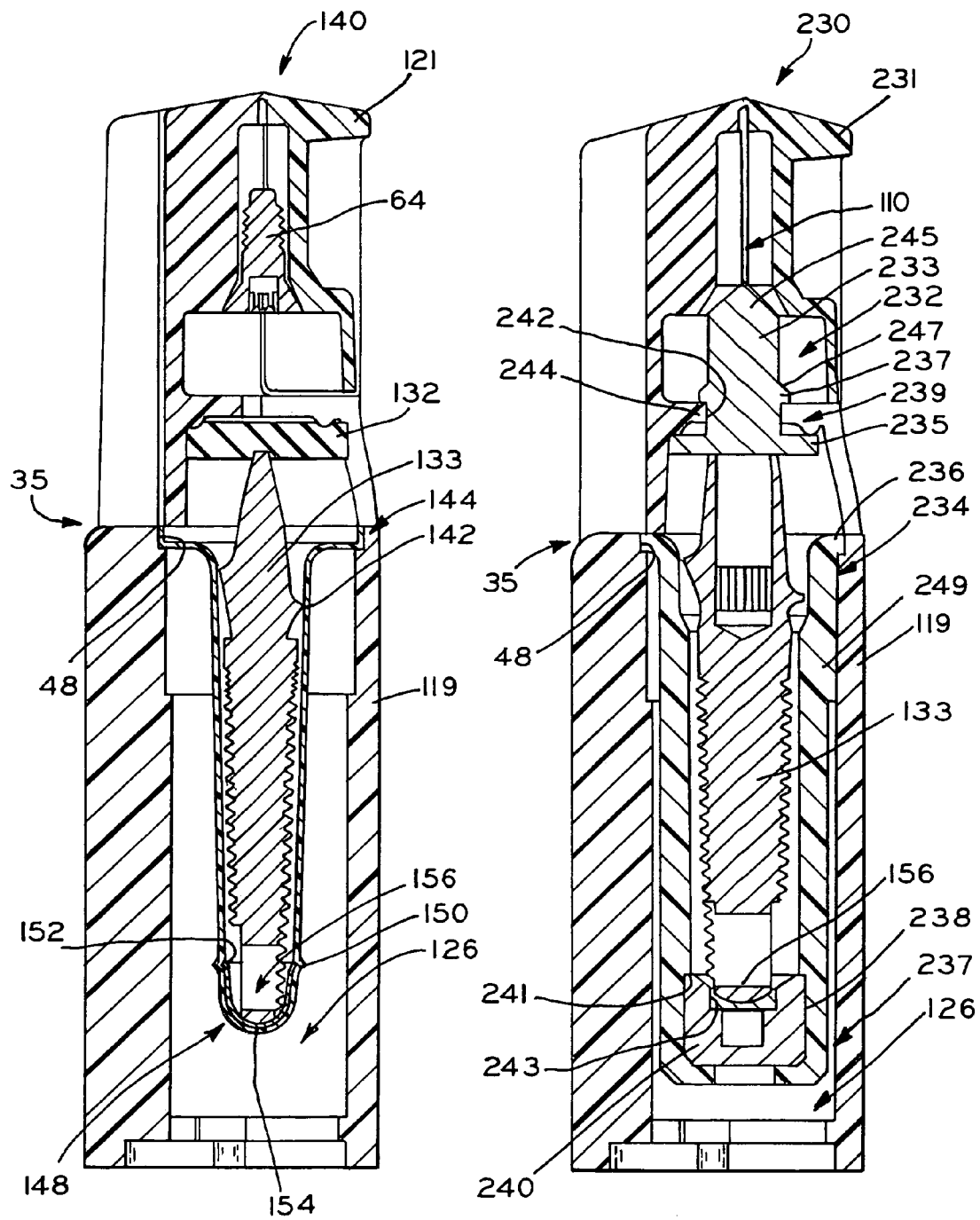
FIG_10    FIG_11

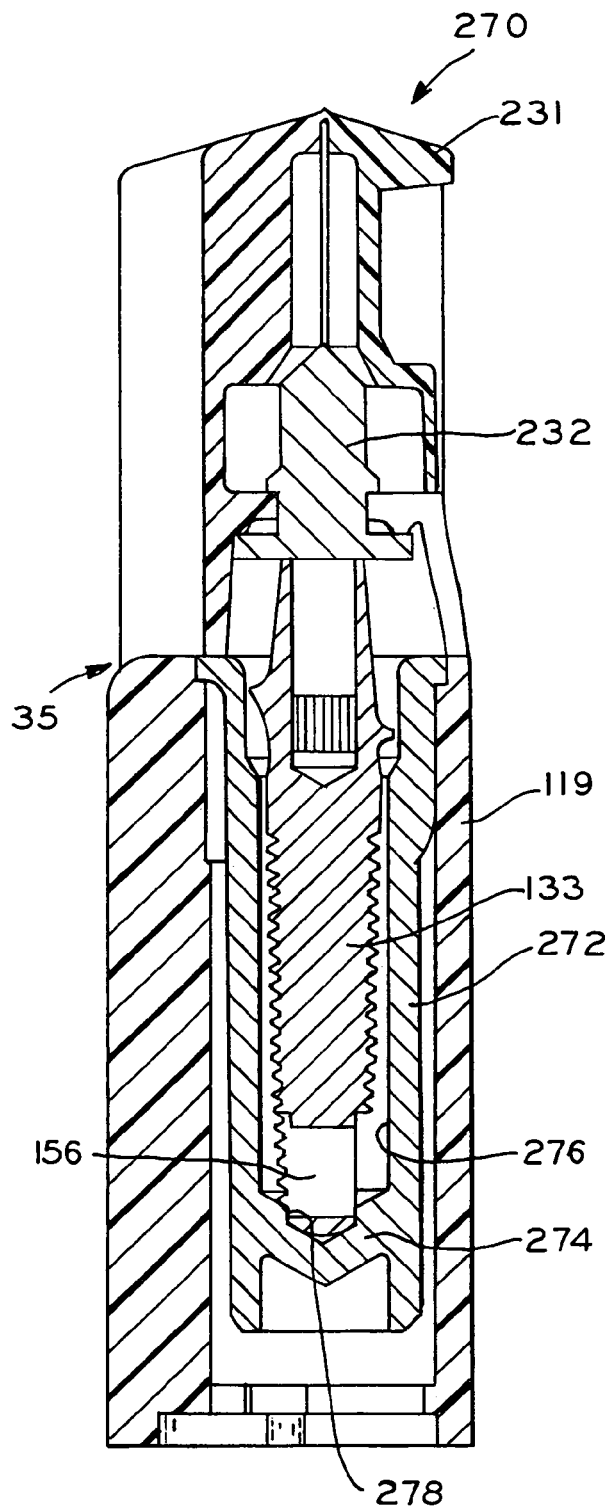
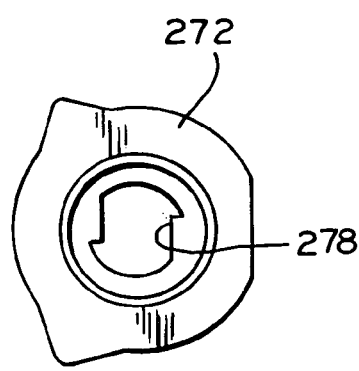
FIG_15
FIG_14

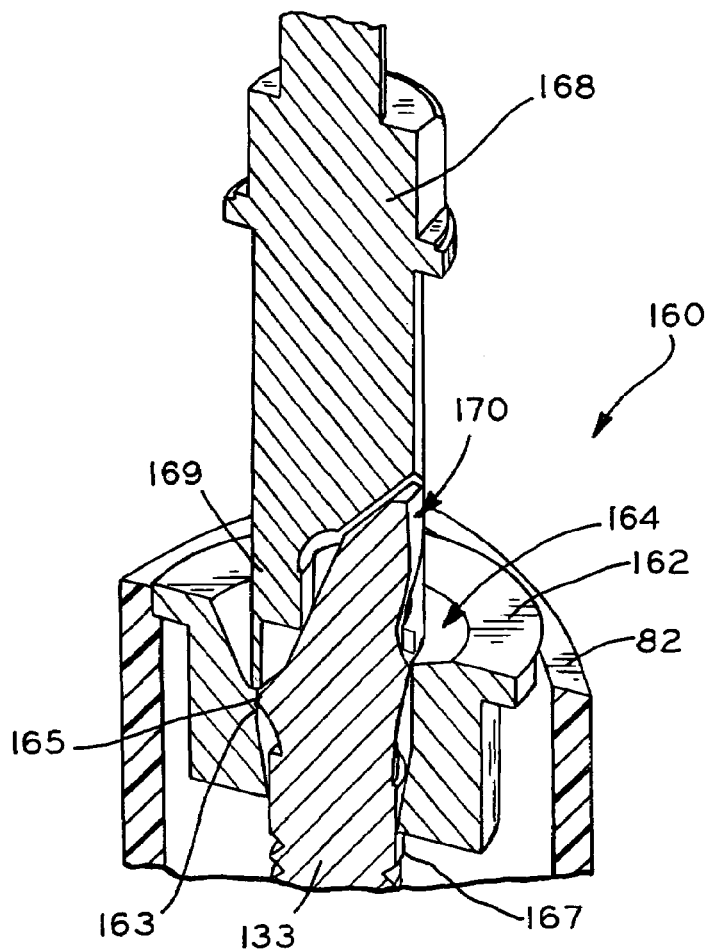
FIG_16
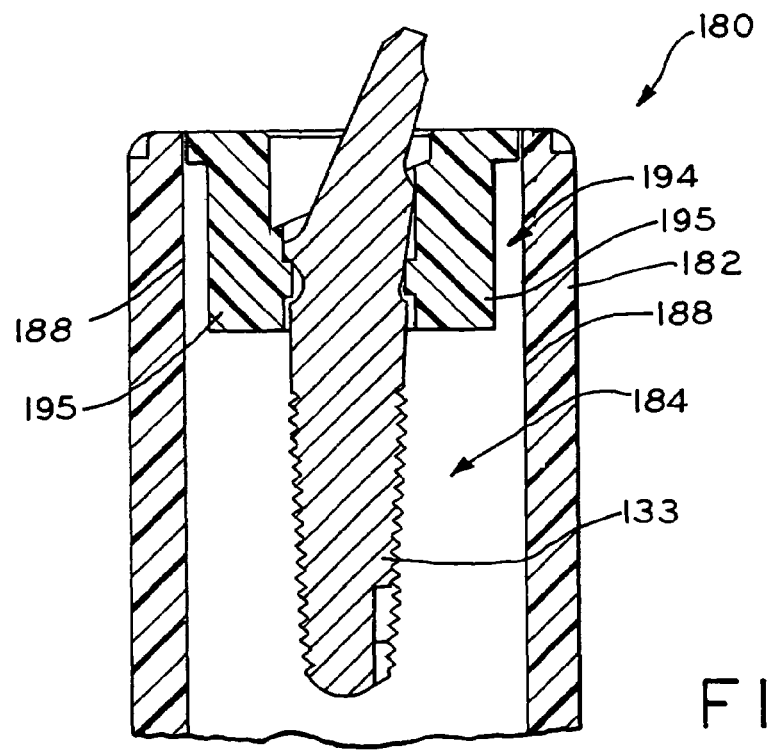
FIG_17

MEDICAL IMPLANT PACKAGE WITH A CAP HAVING A CAVITY

BACKGROUND

1. Field of the Invention

The present invention relates to medical implants, and, more particularly, to packages for housing medical implants.

2. Description of the Prior Art

Generally, medical implants are inserted into a body to restore the function of or replace the anatomy of a patient. It is desirable to present the implants, and components for use therewith, to a surgical site in a sterile, sealed package. In one embodiment, for example, a dental implant and a healing screw are stored within a sterile package until they are removed therefrom and implanted within the mouth of the patient. More specifically, the dental implant, in this embodiment, is removed from the package and threaded into the mandible or maxilla of the patient. Thereafter, the healing screw is inserted into an interior cavity in the implant so that debris or tissue does enter the interior cavity of the implant during the healing process. After the healing process, a prosthesis that replicates a natural tooth is attached to the implant.

What is needed is an improved package that provides a sterile enclosure for, yet provides convenient access to, an implant and the components for use therewith.

SUMMARY

The present invention, in one form, includes a vial and a cap connected by a hinge. The vial includes a cavity for housing at least a portion of a dental implant and, in one embodiment, a plastic sleeve is positioned within the cavity to support the dental implant. In one embodiment, the dental implant is held snugly between the sleeve and an elastic member in the cap. In use, to access the implant, the cap is rotated about the hinge from a closed position to an open position to uncover the implant housed in the vial. In one embodiment, the cap defines a second cavity, separate from the vial cavity, sized and configured to contain a healing screw. In one embodiment, the cap includes two portions connected by a living hinge which define the second cavity. The two cap portions, when moved relative to each other via the living hinge, permit access to the healing screw. In an alternative embodiment, the cap includes two retention members sized and configured to grip the healing screw. To remove the healing screw from the cap, the two retention members are displaced apart from each other by engaging them with a wedge extending from the vial to release their grip on the healing screw.

In one form of the invention, a dental implant package assembly includes a container having a cavity, the cavity configured to receive at least a portion of a dental implant, the container further having a wedge, and a cap movably mounted to the container, the cap having first and second retention surfaces for holding a healing screw, the first and second retention surfaces movable apart from one another upon engagement of the cap with the wedge, wherein the healing screw is removable from the cap when the cap engages the wedge.

In one form of the invention, a dental implant package assembly includes a container having a cavity, the cavity configured to receive at least a portion of a dental implant, a cap fittable to the container, the cap having a cavity configured to contain at least a portion of a healing screw, and a drawer co-operating with the cap to substantially enclose the cavity for containing the healing screw therein. In one embodiment, the drawer of the dental implant package assembly is rotatably mounted to the cap. Further, in one embodiment, one of the cap and the drawer has a projection and the other has a recess for receiving the projection, and wherein the engagement of the recess and the projection defines an axis about which the drawer and the cap may relatively rotate.

In one form of the invention, a dental implant package assembly comprises a container having a cavity, the cavity configured to receive at least a portion of a dental implant, a cap fitted to the container, the cap having a cavity configured to receive at least a portion of a healing screw, the cap including relatively rotatable first and second portions at least partially defining the cavity, wherein relative rotation of the first and second portions provides access to the cavity.

In one form of the invention, in combination, a dental implant having a first end and a second end, and a dental implant package assembly comprising a container having a first contact surface, and a cap having a second contact surface, the cap hingedly mounted to the container, the cap and the container defining a cavity containing the dental implant, the implant held between the first and second contact surfaces, the first end of the dental implant abutting the first contact surface, the second end abutting the second contact surface.

In one form of the invention, a dental implant package assembly includes a container having a cavity, the cavity configured to receive at least a portion of a dental implant, a sleeve having an aperture for receiving the dental implant and a recess for accommodating an instrument attachable to the implant when the implant is positioned in the sleeve.

In one form of the invention, a dental implant package assembly includes a container having a cavity, a sleeve at least partially positioned within the cavity, the sleeve relatively rotatable with respect to the container between first and second positions, and a dental implant, the implant removable from the sleeve in the first position, the implant substantially irremovable from the sleeve in the second position.

In one form of the invention, a dental implant package assembly includes a cap having a first compression surface, a container relatively rotatable with respect to the cap, the container having a cavity for receiving at least a portion of a dental implant, the container further having a second compression surface, and a resilient member positioned between first and second compression surfaces, wherein the cap and container are completely assembled together via relative rotation about an axis for less than one revolution about the axis.

BRIEF DESCRIPTION OF THE DRAWINGS

The above mentioned and other features and objects of this invention, and the manner of attaining them, will become more apparent and the invention itself will be better understood by reference to the following description of exemplary embodiments of the invention taken in conjunction with the accompanying drawings, wherein:

FIG. 5 is a perspective view of the dental implant package of FIG. 4 where the cap has been rotated with respect to the vial via a hinge to an open position;

FIG. 6 is a perspective view of the dental implant package of FIG. 4 where a compartment within the cap has been rotated with respect to the housing of the cap to an access position;

FIG. 7 is a cross-sectional view of a dental implant package cap having first and second portions connected via a living hinge in accordance with an alternative embodiment of the present invention;

FIG. 8 is a cross-sectional view of the cap of FIG. 7 where the second portion has been rotated with respect to the first portion via the living hinge to an access position;

FIG. 9 is a cross-sectional view of a dental implant package in accordance with an alternative embodiment of the present invention;

FIG. 10 is a cross-sectional view of a dental implant package in accordance with an alternative embodiment of the present invention;

FIG. 11 is a cross-sectional view of a dental implant package in accordance with an alternative embodiment of the present invention;

FIG. 14 is a cross-sectional view of a dental implant package in accordance with an alternative embodiment of the present invention;

FIG. 15 is an end view of the sleeve of the dental implant package of FIG. 14;

FIG. 16 is a fragmentary sectional view of a dental implant package in accordance with an alternative embodiment of the present invention;

FIG. 17 is a fragmentary sectional view of a dental implant package having a vial and a sleeve for holding a dental implant in accordance with an alternative embodiment of the present invention;

Figure 1:
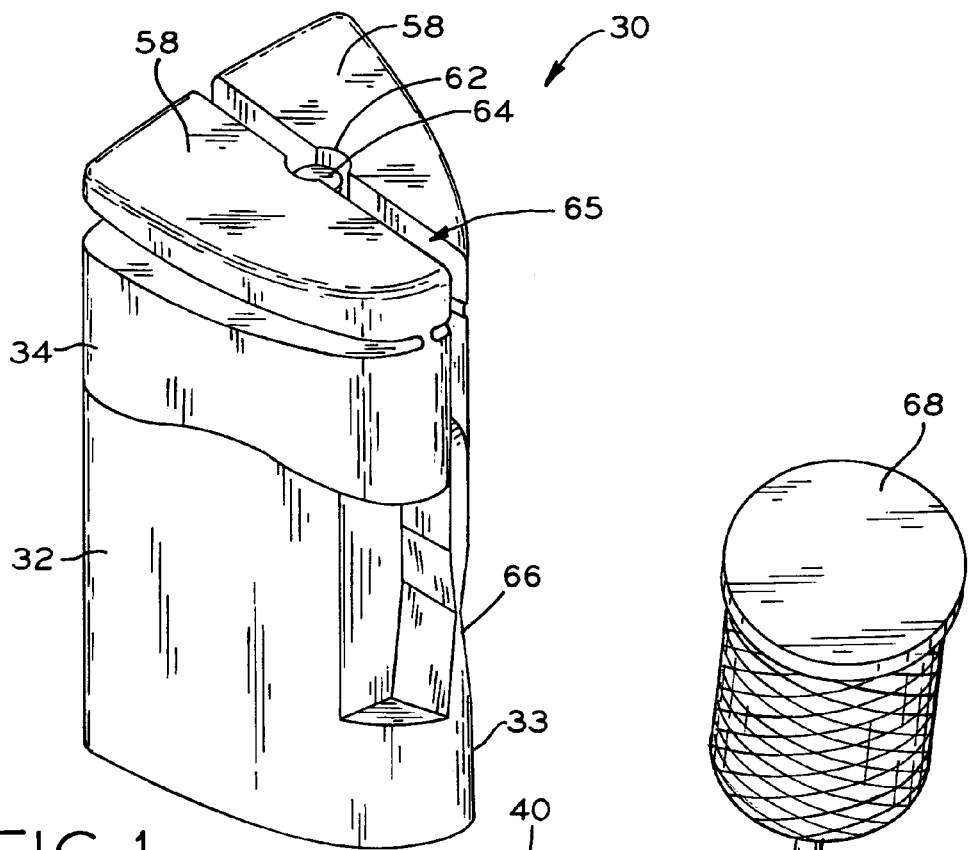
FIG. 1 is a perspective view of a dental implant package having a cap and a vial in accordance with an embodiment of the present invention.

Corresponding reference characters indicate corresponding parts throughout the several views. Although the drawings represent embodiments of the present invention, the drawings are not necessarily to scale and certain features may be exaggerated in order to better illustrate and explain the present invention. The exemplifications set out herein illustrate embodiments of the invention, in one form, and such exemplifications are not to be construed as limiting the scope of the invention in any manner.

DETAILED DESCRIPTION

The embodiments disclosed below are not intended to be exhaustive or limit the invention to the precise forms disclosed in the following detailed description. Rather, the embodiments are chosen and described so that others skilled in the art may utilize its teachings.

Figure 2:
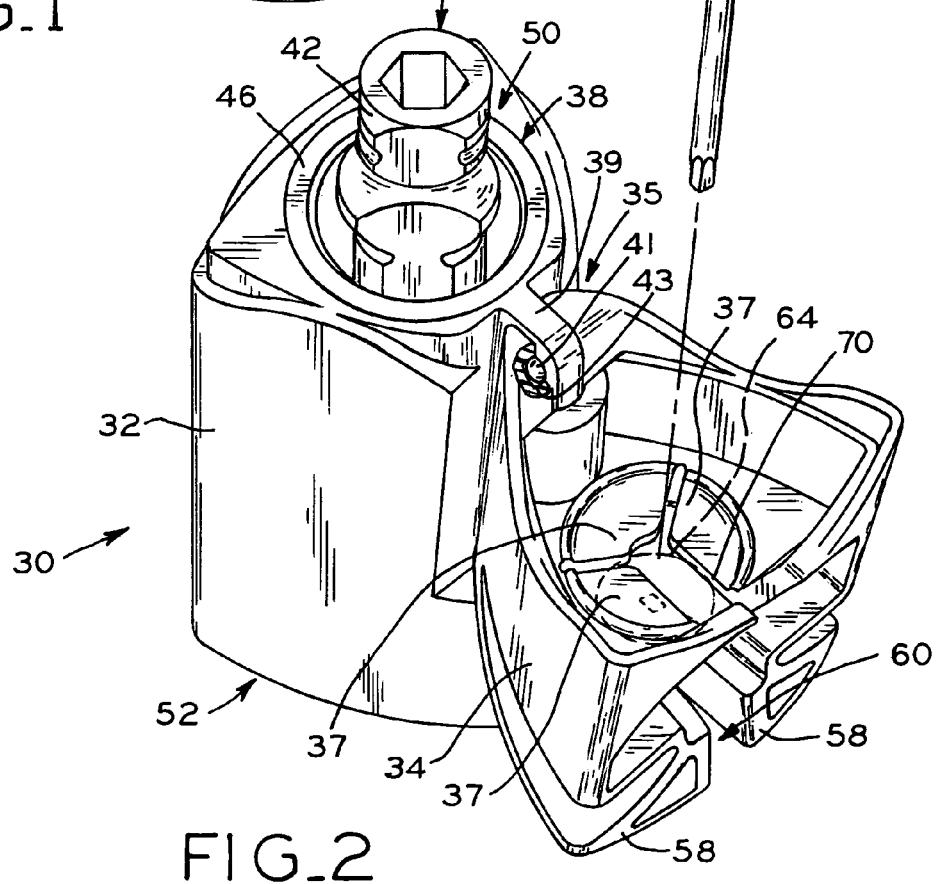
FIG. 2 is a perspective view of the dental implant package of FIG. 1 where the cap has been rotated with respect to the vial via a hinge to an open position.
Figure 3:
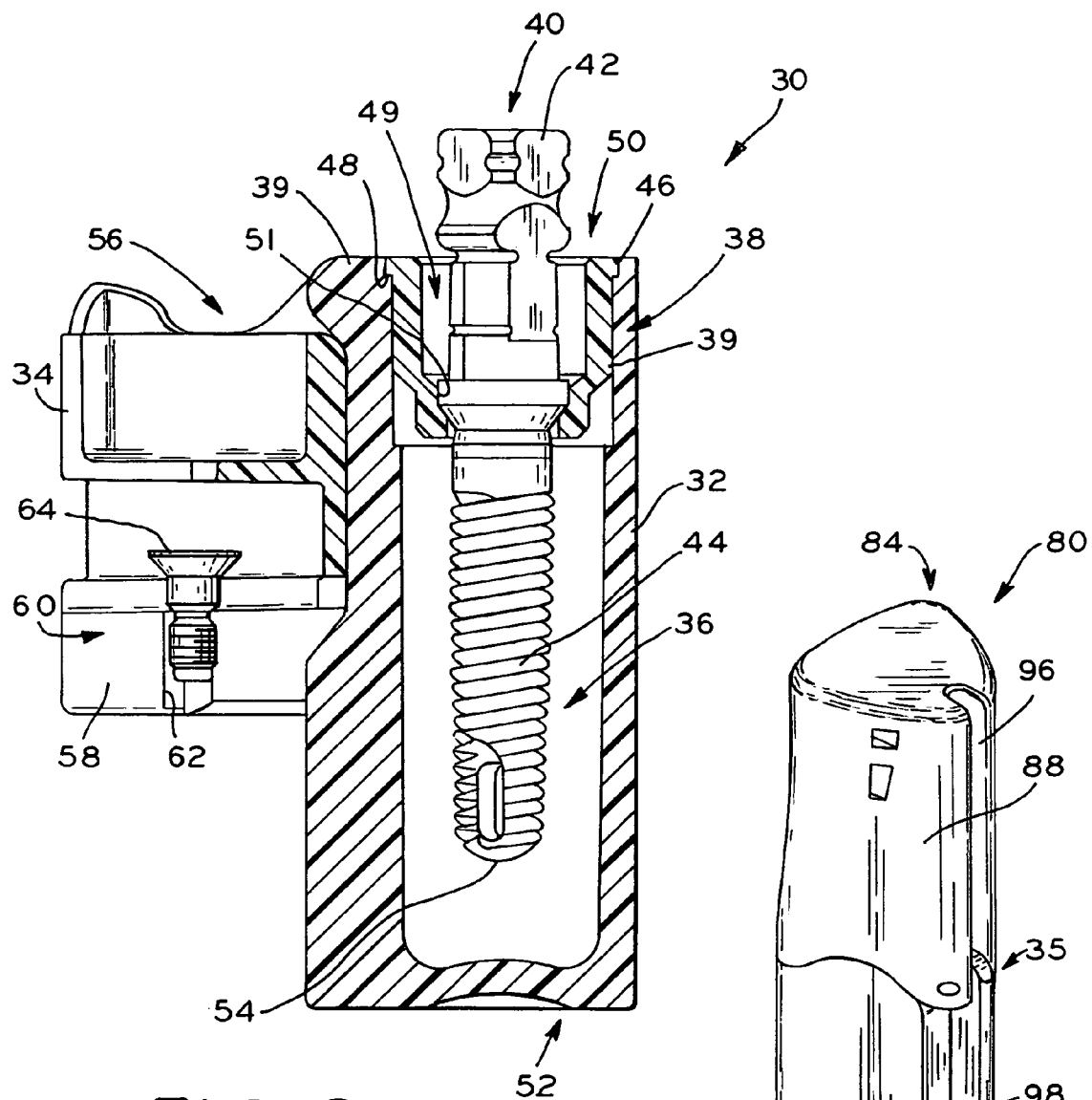
FIG. 3 is a cross-sectional view of the dental implant package of FIG. 1.

Referring to FIGS. 1-3, dental implant package 30 includes vial 32 and cap 34. Vial 32 includes elongate passage 36 (FIG. 3) which is sized and configured to receive sleeve 38 press-fit therein. Vial 32, in this embodiment, has a substantially triangular outer perimeter 33. Advantageously, the triangular perimeter of vial 32 provides a contour that is easier to grip and hold than a round outer perimeter. However, the invention is not limited to such triangular perimeters. Sleeve 38, in this embodiment, includes annular body 39 and lip 46 extending therefrom. Vial 32 further includes recess 48 extending around the perimeter of the upper end of passage 36 at first end 50. When sleeve 38 is press fit into passage 36, lip 46 of sleeve 38 seats within recess 48 and prevents sleeve 38 from traveling further into passage 36.

As illustrated in FIG. 3, sleeve 38 further includes passage 49 having a reduced-diameter portion which defines seat 51. Seat 51 is configured to support dental implant assembly 40 thereon. Dental implant assembly 40, in this embodiment, includes driver mount 42 and implant 44 which are fastened together as an assembly. Dental implant assembly 40 is supported within dental implant package 30 via the interaction of driver mount 42 and sleeve 38. Vial 32 and sleeve 38 are sized, in this embodiment, such that distal end 54 of implant 44 is spaced from second end 52 of vial 32. In this embodiment, first end 50 of vial 32 is open and second end 52 is closed, however, in other embodiments, first and second ends 50 and 52 may both be open, as in the embodiment illustrated in FIG. 6 and described below.

To retain implant assembly 40 within dental implant package 30, cap 34 is positioned over first end 50 of vial 32. Referring to FIG. 2, cap 34 includes spring members 37 which, when cap 34 is in the closed position illustrated in FIG. 1, engage the top of drive mount 42 to elastically bias dental implant assembly 40 against sleeve 38. As a result, dental implant assembly 40 is held snugly in position and is substantially prevented from jostling within the package and creating unwanted rattling sounds. To access implant assembly 40, cap 34 is rotated with respect to vial 32 about hinge 35 from the closed position illustrated in FIG. 1 to the open position illustrated in FIGS. 2 and 3. Hinge 35, in this embodiment, includes base 39, which is integrally molded with vial 32, and projections 41 extending on opposite sides of base 39 which are received within recesses 43 in cap 34. In use, projections 41 resiliently engage and rotate within recesses 43 to allow relative movement between cap 34 and vial 32. In an alternative embodiment, projections may extend from cap 34 and fit within recesses in vial 32.

Cap 34, in the present embodiment, referring to FIGS. 2 and 3, releasably holds a healing screw 64 or other component therein. More particularly, cap 34 includes retention members 58 which define retention recess 62. Retention members 58 are elastically biased against healing screw 64 such that the sides of retention recess 62 bear against healing screw 64. In use, when cap 34 is pivoted about hinge 35 into the open position illustrated in FIG. 2, recess 65 of cap 34, which is defined by retention members 58, receives wedge 66 of vial 32. Wedge 66 is sized and configured such that it engages the sides of recess 65 when cap 34 is opened to cause retention portions 58 to splay apart, or move outwardly, from each other. As a result, retention recess 62 expands such that healing screw 64 can be easily removed therefrom. In the present embodiment, to remove healing screw 64, referring to FIG. 2, instrument 68 is inserted through slot 70 in cap 34 to engage healing screw 64. Thereafter, instrument 68 and healing screw 64 are moved laterally through removal passage 60.

Figure 4:
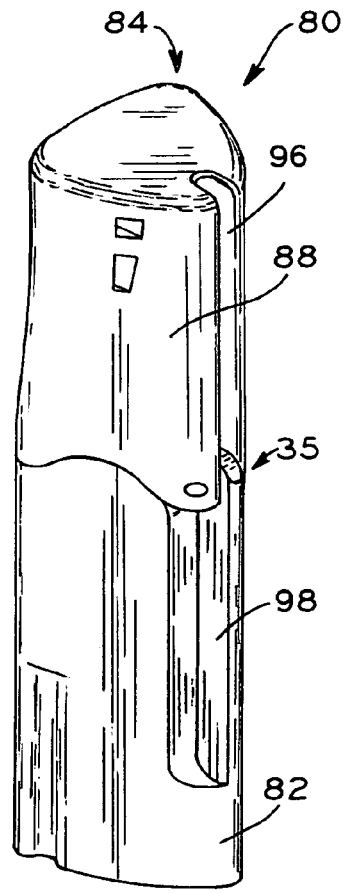
FIG. 4 is a perspective view of a dental implant package having a cap and a vial in accordance with an alternative embodiment of the present invention.

In an alternative embodiment, referring to FIGS. 4-6, dental implant package 80 includes vial 82 and cap 84 connected via hinge 35. Cap 84 includes housing 88 and drawer compartment 90 rotatably connected to housing 88 via hinge 92. In this embodiment, compartment 90 is moved between a closed position illustrated in FIG. 5 and an open position illustrated in FIG. 6. The travel of compartment 90 with respect to housing 88, referring to FIG. 5, is guided and limited by the interaction of projection 91 extending from compartment 90 and groove 93 in housing 88. In the closed position (FIG. 5), healing screw 64 or other component is contained within a cavity defined by housing 88 and compartment 90. In use, to access healing screw 64, compartment 90 is rotated with respect to housing 88 to its open position (FIG. 6). In this embodiment, instrument 68 is inserted through slot 94 in housing 88 and is engaged with healing screw 64. Instrument 68 is then used to rotate compartment 90 with respect to housing 88, as illustrated in FIG. 6. Thereafter, healing screw 64 is removed from the cavity.

Referring to FIG. 4, vial 82 also includes spline 98 which facilitates the alignment of cap 84 with vial 82 when cap 84 is moved from the closed position illustrated in FIG. 4 to the open position illustrated in FIG. 5. More particularly, cap 84 includes groove 96 extending along the length thereof which, when cap 84 is moved into the open position (FIG. 5), receives spline 98. The interaction of groove 96 and spline 98 reduces the potential for relative movement between vial 82 and cap 84, especially when compartment 90 is being moved relative to cap housing 88 and when healing screw 64 is being removed from cap 84.

Referring to the alternative embodiment illustrated in FIGS. 7 and 8, dental implant package 100 includes cap 102. Cap 102 includes first portion 104 rotatably connected to second portion 106 via living hinge 108. Living hinge 108, in this embodiment, comprises a thin portion of material connecting first and second portions 104 and 106. When first portion 104 and second portion 106 are in close opposition to each other, as illustrated in FIG. 7, they define cavity 110 which is sized and configured to house healing screw 64. In this embodiment, healing screw 64 or other component is loosely positioned within cavity 110, however, in alternative embodiments, healing screw 64 can be wedged between and held in a substantially constant position by first and second portions 104 and 106. In the present embodiment, second portion 106 includes projections 111 extending therefrom which are received in recesses 112 of first portion 104 to releasably hold first and second portions 104 and 106 together in a closed position. In one embodiment, projections 111 and recesses 112 provide a releasable snap-fit between first portion 104 and second portion 106. To access healing screw 64, second portion 106 is rotated with respect to first portion 104 about hinge 108. More particularly, with cap 102 in an open position, in this embodiment, instrument 68 is inserted through slot 110 in cap 102 and engaged with healing screw 64. Instrument 68 is then rotated outwardly to move second portion 106 into the open position illustrated in FIG. 8.

Referring to the embodiment illustrated in FIG. 9, dental implant package 120 includes vial 119 having passage 126 and cap 121 connected to vial 119 via hinge 35. Dental implant package 120 further includes sleeve 122 positioned within passage 126 at first end 124 and stop 128 positioned at second end 130 of passage 126. Stop 128, in this embodiment, is sized and configured such that arms 134 of stop 128 are resiliently biased against the walls of passage 126. Arms 134 are also configured to engage projections 136 extending from the walls of interior passage 126 to provide a support for stop 128 so that stop 128 is maintained in a substantially fixed position within passage 126. Dental implant package 120 further includes elastomeric disk 132 positioned in recess 123 of cap 121. In the closed position of cap 121, implant 133 is resiliently held between disk 132 and stop 128. Advantageously, implant 133 is held snugly within dental implant package 120 such that it does not rattle therein. Sleeve 122, in this embodiment, may not engage implant 133, but rather, it may surround implant 133 to prevent large relative movements thereof.

Referring to the alternative embodiment illustrated in FIG. 10, dental implant package 140 includes vial 119 and cap 121 connected via hinge 35 similar to those described above. Dental implant package 140 further includes sleeve 142 positioned in passage 126 of vial 82 and, similar to the embodiment of FIG. 9, elastomeric disk 132 positioned in cap 121. Sleeve 142 includes a first end 144 which is received within recess 48 of vial 82. Sleeve 142 further includes a second end 148 opposite first end 144 which includes annular recess 150 sized for receiving lip 152 of titanium cup 154 to retain titanium cup 154 in second end 148. In use, implant 133 is held in position between elastomeric disk 132 and titanium cup 154 such that distal end 156 of implant 133 does not contact the surface of sleeve 142. Advantageously, similar to the embodiment described above, implant 133 is held snugly in place within package 140 by elastomeric disk 132.

Referring to the alternative embodiment illustrated in FIG. 11, dental implant package 230 includes vial 119 and cap 231 connected via hinge 35 similar to those described above. Dental implant package 230 further includes plug 232 positioned in cap 231 and sleeve 234 positioned in passage 126 of vial 119. Plug 232, in this embodiment, includes integral shaft 233 and head 235. Shaft 233 includes annular rim 237 extending around the perimeter of shaft 233 which defines gap 239 between rim 237 and head 235. In use, plug 232 is press-fit, or snap-fit, into cap 231 such that, in this embodiment, plug 232 is substantially irremovable during the ordinary use of dental implant package 230. More particularly, shaft 233 of plug 232 is inserted through slot 242 of cap 231 until rim 237 engages the sides of slot 242. The diameter of rim 237 is larger than slot 242 such that, when rim 237 is pushed through slot 242, portion 244 of cap 231 surrounding slot 242 deflects to accommodate rim 237. After rim 237 has passed through slot 242, portion 244 substantially resiliently returns to its original position and is tightly interfitted with shaft 233. Further, after rim 237 has passed through slot 242, portion 244 is tightly interfitted within gap 239. To facilitate the insertion of plug 232 into slot 242, plug 232 has beveled surfaces 245 and 247 which provide a gradual lead-in to guide plug 232 into recess 242. In this embodiment, plug 232 extends into cavity 110 of cap 231 such that a healing screw, such as healing screw 64, cannot be positioned therein.

Sleeve 234 includes first end 236 and is sized and configured to be received within recess 48 of vial 82. Sleeve 234 further includes crush-ribs 249 which extend longitudinally along the outside surface of sleeve 234. Crush-ribs 249 are sized and configured such that when sleeve 234 is inserted into recess 48 of vial 82, crush-ribs 249 can elastically and/or plastically deform to create a tight fit between sleeve 234 and vial 82. Sleeve 234 further includes a second end 237 opposite first end 236 which includes an enlarged-diameter portion 238 sized for receiving titanium plug 240. Enlarged-diameter portion 238 of sleeve 234 includes ledge 241 which overlaps a portion of titanium plug 240 to retain plug 240 in second end 237 of sleeve 234. In this embodiment, plug 240 includes recess 243 which is sized and configured to closely receive distal end 156 of implant 133. Similar to dental implant package 140, implant 133 is held in position by cap plug 232 and titanium plug 240 such that distal end 156 of implant 133 does not substantially contact the surface of sleeve 234.

Figure 12:
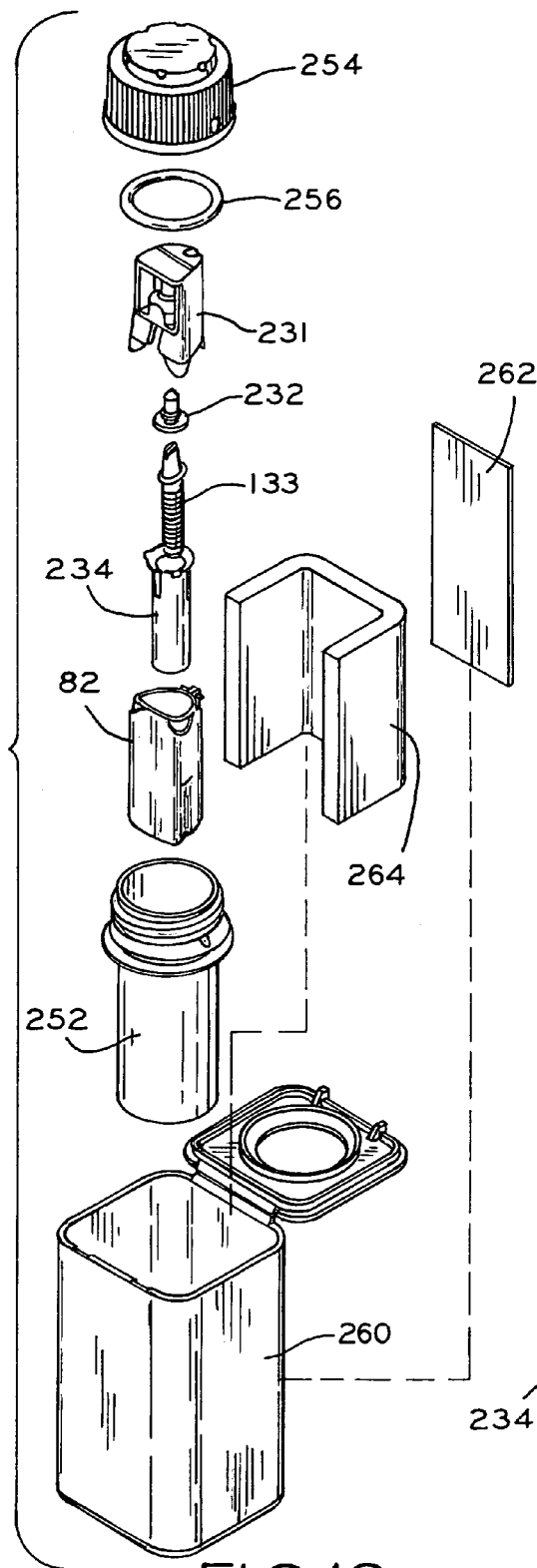
FIG. 12 is an exploded view of the dental implant package of FIG. 11, an outer package, and a container for housing the dental implant package.
Figure 13:
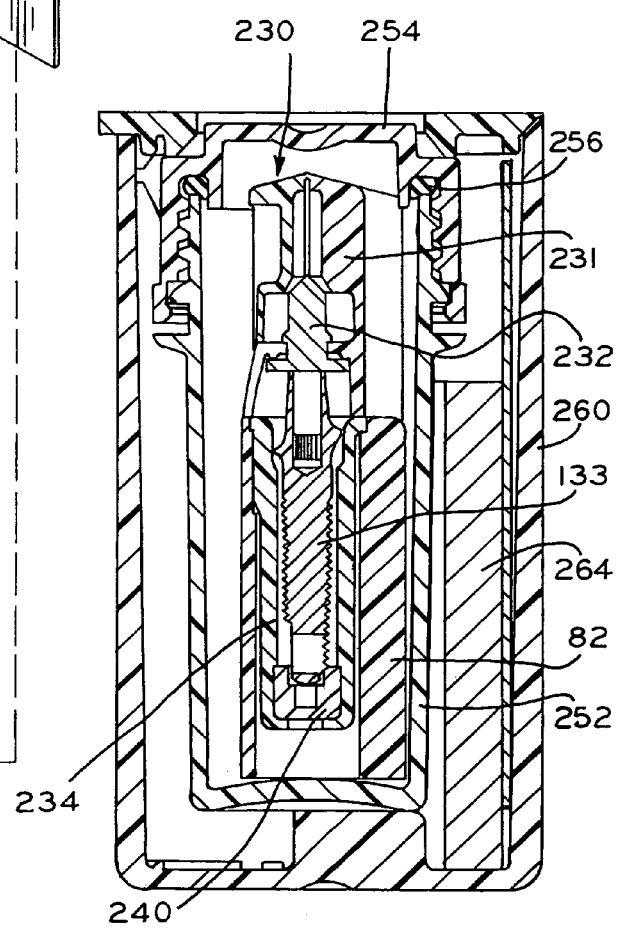
FIG. 13 is a sectional view of the dental implant package of FIG. 11 positioned within the outer package and container.

In some embodiments, referring to FIGS. 12 and 13, the dental implant packages disclosed herein, such as dental implant package 230, may be inserted into a hermetically-sealed outer package to prevent contamination of the implant and healing screw contained therein. The outer package, in this embodiment, includes outer vial 252, cap 254 and seal 256 positioned intermediate outer vial 252 and cap 254. Once dental implant package 230 has been positioned within outer vial 252, cap 254 is screwed onto outer vial 252 via threads 258 compressing seal 256 therebetween to create a substantially air-tight seal. In some embodiments, it is desirable to present the sealed outer package within an outer container, such as container 260. Container 260, in this embodiment, is substantially square and includes many large surfaces upon which stickers and identifying labels, such as labels 262, may be positioned thereon. In this embodiment, container 260 is also sized to house a folded set of printed instructions 264 which describe methods for using the dental implant package and implant contained therein.

Referring to the alternative embodiment illustrated in FIGS. 14-15, dental implant package 270 includes vial 119 and cap 231 connected via hinge 35, and sleeve 272 positioned in vial 119. Unlike dental implant package 230, implant package 270 does not include a titanium plug 240 nor does sleeve 272 have an enlarged-diameter portion sized for receiving a titanium plug 240. Rather, sleeve 272 has an integrally-molded support 274 that extends between annular side walls 276 which is sized and configured to support dental implant 133 thereon. More particularly, support 274 includes recess 278 which is contoured to replicate the end geometry of, and to thereby closely receive distal end 156 of implant 133 such that implant 133 cannot substantially rotate with respect to sleeve 272. In use, advantageously, recess 278 prevents implant 133 from rotating when an instrument is attached to the top of implant 133. When cap 231 is moved into a closed position over vial 119, implant 133 is held between support 274 and plug 232 positioned in cap 231. To accommodate implant 133 of different lengths, several different embodiments of sleeve 272 can be made wherein the position of support 274 with respect to end 280 can be different to accommodate implants 133.

Referring to the embodiment illustrated in FIG. 16, dental implant package 160 includes vial 82 and sleeve 162 positioned therein. Sleeve 162 includes an interior recess 164 extending therethrough sized for receiving and supporting implant 133 therein. In this embodiment, sleeve 162 includes a substantially rectangular pocket 163 surrounding margin 165 of implant 133 to substantially prevent horizontal movement of implant 133 within sleeve 162. Sleeve 162 further includes a contact surface, or corner 167, at the bottom of recess 164 which contacts and supports, or releasably engages, implant 133. Recess 164 is also sized and configured to allow distal end 169 of drive instrument 168 to be positioned over proximal end 170 of implant 133 while implant 133 is seated within recess 161. Recess 164 permits drive instrument 168 to be connected to implant 133 without requiring a dentist to manually remove and handle implant 133.

Figures 18, 19:
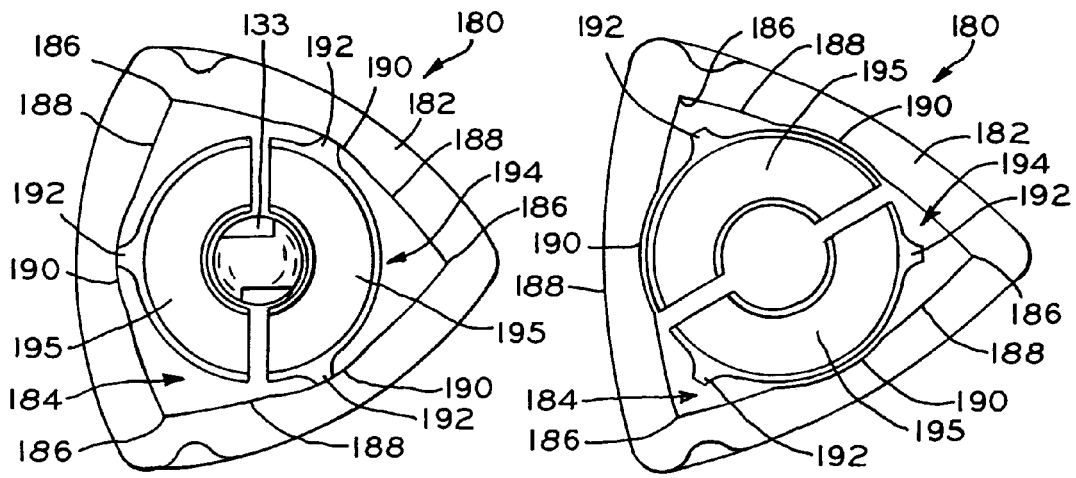
FIG. 18 is an end view of the dental implant package of FIG. 17.
FIG. 19 is an end view of the dental implant package of FIG. 17 where the sleeve has been rotated with respect to the vial to allow the implant to be removed.

Referring to the embodiment in FIGS. 17-18, dental implant package 180 includes vial 182 and sleeve 194 positioned in triangular inner passage 184 of vial 182. In use, sleeve 194 is rotatable between a first position (FIG. 18) in which it grips and holds implant 133 and a second position (FIG. 19) in which implant 133 can be easily removed from sleeve 194. Inner passage 184 of vial 182 is defined by walls 188 which intersect at vertices 186. Each wall 188 includes a recess 190 for frictional engagement by one of projections 192 extending from sleeve 194, as shown in FIG. 18. More particularly, projections 192 are engaged with walls 188 in an interference-fit relationship. Owing to the interference-fit relationship, gripping arms 195 of sleeve 194 are biased against implant 133 to apply a gripping force thereto. In this embodiment, the gripping force applied to implant 133 is sufficient to hold implant 133 snugly in place and to substantially prevent it from being prematurely removed from the package. To remove implant 133 from the dental implant package, sleeve 194 is moved into its second position, as illustrated in FIG. 19. In this position, projections 192 are no longer engaged with walls 188 and gripping arms 195 of sleeve 194 are free to resiliently move apart from each other. As a result, the gripping force applied by gripping arms 195 on implant 133 is sufficiently reduced to allow implant 133 to be easily removed from sleeve 194. In the present embodiment, an instrument is placed over the distal end of implant 133 to turn implant 133 and sleeve 194 until sleeve 194 releases its grip on implant 133. Also, in the present embodiment, recesses 190 in walls 188 assist in keeping sleeve 194 in the position illustrated in FIG. 18 and prevent sleeve 194 from being prematurely turned.

Figure 21:
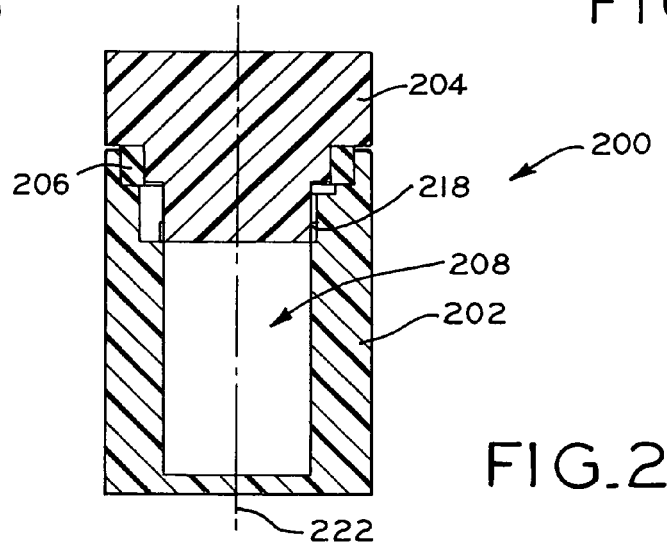
FIG. 21 is a cross-sectional view of the dental implant package of FIG. 20.
Figure 20:
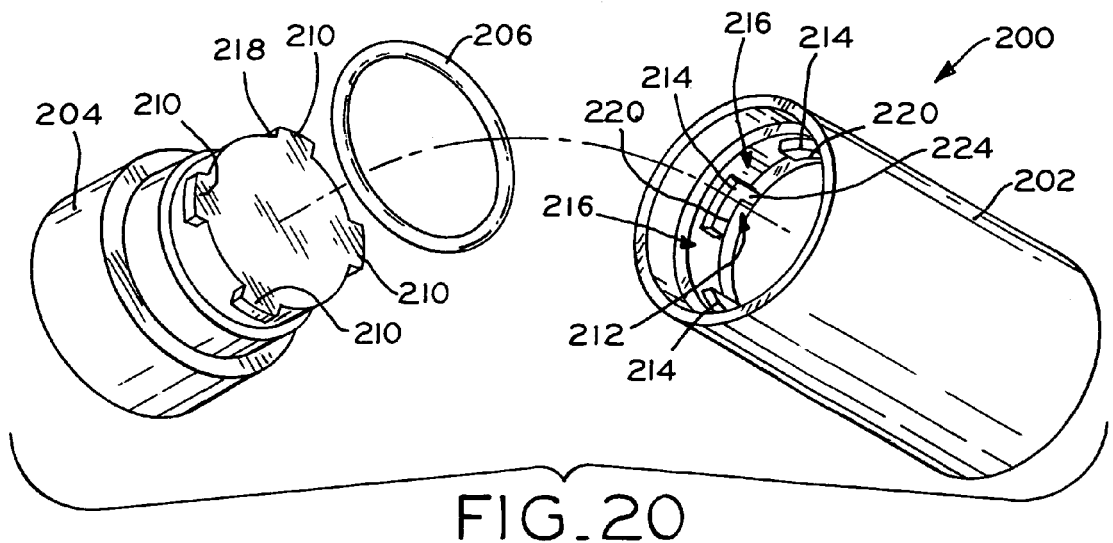
FIG. 20 is an exploded view of a dental implant package in accordance with an alternative embodiment of the present invention.

Referring to FIGS. 20 and 21, dental implant package 200 includes vial 202, cap 204 and seal 206 positioned intermediate vial 202 and cap 204. Vial 202 and cap 204, when assembled, define cavity 208 which is sized and configured to house a dental implant. Cap 204, in this embodiment, can be assembled to vial 202 by turning cap 204 less than 360° to create an air-tight seal between cap 204 and vial 202 by compressing seal 206 therebetween. More particularly, cap 204 includes projections 210 extending therefrom which are sized and configured to be received in recesses 212 of vial 202. Referring to FIG. 20, each recess 212 of vial 202 is defined by a substantially L-shaped projection 214. To assemble cap 204 to vial 202, projections 210 extending from cap 204 are inserted into gaps 216 between adjacent L-shaped projections 214. As cap 204 is being inserted into cavity 208, seal 206 is compressed between vial 202 and cap 204. Cap 204 is inserted into cavity 208 until top surfaces 218 of projections 210 are positioned beneath contact surfaces 220 of L-shaped portions 214. Thereafter, cap 204 is rotated about longitudinal axis 222 of vial 202 until at least a portion of projections 210 are positioned under at least a portion of L-shaped projections 214. Once assembled, surfaces 218 of projections 210 are elastically biased against contact surfaces 220 of projections 214 by the compressed seal 206 positioned between cap 204 and vial 202. As a result of the above, cap 204 can be quickly assembled to and disassembled from vial 202 to reduce the time required to remove the implant from the package. Also, in this embodiment, the rotation of cap 204 with respect to 202 is limited by stops 224 of L-shaped projections 214 such that cap 204 is turned less than a quarter-turn.

While this invention has been described as having an exemplary design, the present invention may be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains.

What is claimed is:
1. A dental implant package assembly, comprising
a container having a cavity, said cavity specifically configured to receive at least a portion of a dental implant;
a cap fitted to said container, said cap having a cap cavity configured to receive at least a portion of a healing component, the cap cavity being shaped to generally correspond to the shape of the healing component, said cap including a first portion and a second portion cooperatively, and at least partially, defining said cap cavity;

a first connector movably connecting the first portion to the container; and a second connector rotatably connecting the second portion to the first portion so that rotation of the second portion relative to the first portion provides access to the healing component disposed within the cap, the second connector being a living hinge.

2. The dental implant package assembly of claim 1, wherein said second connector includes a hinge portion.

3. The dental implant package assembly of claim 1, wherein said cap is hingedly mounted to said container by said first connector.

4. The dental implant package assembly of claim 1, wherein one of said first portion and said second portion includes a projection and the other of said first portion and said second portion includes a recess sized and configured for receiving said projection, said projection and said recess providing a releasable snap-fit between said first portion and said second portion.

5. The dental implant package of claim 1 wherein the cap further comprises two opposite end portions, and wherein the first and second connectors are disposed at different ones of the opposite end portions.

6. A dental implant package, comprising:

a container specifically configured for holding a dental implant;

a cap at least partially removably mounted on the container and having an interior shape generally corresponding to the shape of at least a portion of a healing component for holding the healing component, the cap having two distinct parts including a first part and a second part at least partially detachable from the first part;

a first hinge connecting the cap to the container; and a second hinge connecting the first part to the second part.

7. The dental implant package of claim 6 wherein the second hinge is a living hinge.

8. The dental implant package of claim 6 wherein the cap has two opposite end portions, the first hinge being on one of the opposite end portions and the second hinge being on the other opposite end portion.

9. The dental implant package of claim 6 wherein the cap has an upper end portion and a lower end portion configured for opposing the container, and wherein the first hinge is disposed on the lower end portion and the second hinge is disposed on the upper end portion.

10. The dental implant package of claim 9 wherein the second part forms a movable sidewall of the cap for providing access to the healing component.

11. A dental implant package, comprising:

a container specifically configured for holding a dental implant and defining a main opening;

a cap removably mounted on the container for covering and uncovering the opening and configured for specifically holding a healing component, the cap including:

a top surface, a generally cylindrical side surface forming a side of the cap and extending downward from the top surface, a first portion, and a second portion rotatably attached to the first portion and forming at least part of the cylindrical side surface so that rotation of the second portion relative to the first portion forms an opening on the cylindrical side surface for access to the healing component through the cylindrical side surface.

12. The dental implant package of claim 11 wherein the first portion is connected to the second portion by a living hinge.

13. The dental package of claim 11 wherein the cap further includes a cavity shaped to generally correspond to at least part of the shape of a healing component for holding the healing component.

* * * * *